US005792202A

United States Patent [19]
Rueter

[11] Patent Number: 5,792,202
[45] Date of Patent: Aug. 11, 1998

[54] SYSTEM AND METHOD FOR RATE ENCODING OF PACING INTERVALS FOR EXTERNAL TRANSMISSION OF DATA

[75] Inventor: John C. Rueter, Shoreview, Minn.

[73] Assignee: Medtronic, Inc., Minneapolis, Minn.

[21] Appl. No.: 761,031

[22] Filed: Dec. 5, 1996

[51] Int. Cl.$^6$ ...................................................... A61N 1/36
[52] U.S. Cl. ............................................... 607/27; 607/32
[58] Field of Search ................................. 607/27, 30, 32, 607/60

[56] References Cited

U.S. PATENT DOCUMENTS

| | | |
|---|---|---|
| 4,190,055 | 2/1980 | Walters . |
| 4,522,208 | 6/1985 | Buffett . |
| 4,665,919 | 5/1987 | Mensink . |

*Primary Examiner*—Scott M. Getzow
*Attorney, Agent, or Firm*—Harold R. Patton; Michael B. Atlass

[57] ABSTRACT

There is provided a system and method for increased data transmission from an implanted pacemaker when the pacemaker is in magnet mode. Pacemaker data including, e.g., pacemaker operating conditions, pacing events and patient events, is outputted by changing the asynchronous pacing rate to selected ones of available rates, and with a predetermined sequence, enabling read out of the data on an EKG strip chart. In a preferred embodiment, data-encoded pace pulses with intervals corresponding to selected rates are delivered in a predetermined sequence with fixed rate non-data intervals. For example, four pulses are delivered at 85 ppm followed by one or more data-encoded pulses, each data-encoded pulse being at 90, 95 or 100 ppm, whereafter the sequence is repeated with additional data-encoded intervals. The combination of rates for each of the data-encoded intervals represents the pacemaker data, and can be decoded by observing an EKG strip taken during the pattern of pace pulses. The invention provides for enhanced data transmission from an implanted pacemaker without the need of a programmer for receiving the data, and is thus particularly useful in environments where only a simple magnet is available for pacemaker follow-up.

16 Claims, 5 Drawing Sheets

SYSTEM AND METHOD FOR RATE ENCODING OF PACING INTERVALS FOR EXTERNAL TRANSMISSION OF DATA

FIELD OF THE INVENTION

This invention relates to cardiac pacemaker systems and, more particularly, systems which change pacing mode in response to an external signal for the purpose of transmitting information.

BACKGROUND OF THE INVENTION

Modern cardiac pacemaker systems have become increasingly sophisticated, both in terms of functions that can be carried out and transmission of information to and from an implanted pacemaker. Thus, the exemplary modern pacemaker incorporates microprocessor-based control, and RF telemetry between the implanted pacemaker and an external programmer unit. The telemetry enables transmission of programming instructions to the implanted pacemaker, as well as downloading data to the pacemaker and uploading collected data from the pacemaker back to the external programmer. Particularly for high end or premium-type pacemakers, a great deal of data concerning the operating conditions of the pacemaker and collected diagnostic data can be obtained through the system RF-uplink or upload capability, as long as the physician has the requisite external programmer unit. Some of this information is vital, and must be obtained by the physician periodically. Examples of pacemaker operating conditions which need to be periodically monitored are remaining battery life and lead integrity. Diagnostic or patient event data which is of interest to the physician includes whether or not there have been episodes of atrial or ventricular tachycardia; percentage of cycles for a dual chamber pacemaker where atrial senses are tracked; patient rate history, suitably in histogram form; number of PVCs; number of undersenses; etc.

As long as the pacemaker has such telemetry capability and the attending physician has the required programmer, all of the data that has been collected by the pacemaker can be uploaded as desired. However, in many cases today, throughout the world, the physician either does not have the programmer, or is unwilling to use it. Indeed, it is the case that a significant percentage of pacemaker follow-ups are still done without a programmer, i.e., with the physician using only a magnet to initiate one or two simple pacemaker tests, or to reprogram a limited number of pacemaker variables. It has long been known in the pacing art to design an implantable pacemaker to react to a magnet signal in a manner designed so that the attending physician can monitor the subsequent pacing on an EKG strip, and determine a limited amount of information. Thus, placement of a magnet in the vicinity of a pacemaker places the pacemaker into a magnet mode, wherein the pacemaker operates at a fixed rate which contains information representative of a specific operating condition. For example, the pacemaker may respond by pacing at a fixed rate with a voltage level which is adjusted to one of two or three values to represent battery condition, e.g., whether or not the battery has reached a designated "end-of-life" value. Alternately, a received magnet signal may initiate a threshold test, well known in the art, whereby the pace pulse amplitude is varied in amplitude through a range so as to provide an indication on an EKG strip of when a pulse does not capture the heart, thereby indicating threshold. Generally, this information is been outputted just one time, such that if the beginning of the EKG strip is missed, the information is not presented. Thus, to date, pacemakers have provided for rather limited data transmission by adjustment of pace pulses in response to a magnet signal.

The prior art shows several examples of magnet mode operation, wherein a delay is added to an interval to indicate a condition or logic state. In U.S. Pat. No. 4,190,055, the pacemaker is provided with a circuit for indicating the contents of a register which controls parameters associated with the pacemaker. Data from the register is shifted through a parallel to serial converter, and a delay is added between pace pulses when a first logic state (e.g., logic 1) appears, and no delay is added when the other logic state (e.g., a logic 0) appears. By this arrangement, the parameter states can be determined externally by observing the successive periods between pace pulses when the pacemaker is in its magnetic mode. In U.S. Pat. No. 4,522,208, there is shown another form of pulse position modulation, whereby a parameter value is encoded by shifting the position of the middle one of three consecutive pace pulses, the shift direction and amount being controlled to indicate the parameter value. However, while these exemplary arrangements disclose pacemaker designs for outputting data during magnet mode operation, they provide for only very limited data flow. What is desirable is an improved capability of transmitting greater amounts of data in magnet mode, e.g., more than one or two condition states, and preferably in a manner so that it can be discerned easily by a physician examining an EKG strip.

SUMMARY OF THE INVENTION

A pacemaker system and method are provided for generating pacing pulses at encoded rates during magnet mode, with an encoding scheme which enables transmission of significant data that can be determined by observing an EKG strip, or which can be automatically decoded. The data encoding scheme provides for a pattern of pacing intervals, each interval corresponding to a pacing rate, wherein one or more intervals at selected rates are interspersed with intervals at a predetermined rate; the selected rate intervals are encoded independently by adjusting each of said intervals to one of a plurality of discrete rates, whereby each encoded interval independently carries data, and the sequences represent data that had been stored in the pacemaker. In an illustrative preferred embodiment, a first group of successive intervals, e.g., four, comprise pace pulses at a given magnet rate, followed by a second group of successive intervals , each interval in the second group being encoded with a selected one of a set of different rates. Thus, for example, a sequence may consist of four successive intervals at a rate of 85 bpm, followed by two successive intervals encoded with one of four different rates (90, 95, 100 and 105), whereafter another sequence is transmitted until all of the desired information is transmitted. The encoded information may identify one or more conditions such as atrial tachycardia, or ventricular tachycardia, followed by subsequent data providing more specific information concerning the condition.

DETAILED DESCRIPTION OF THE PREFERRED EMBODIMENTS

Figure 1:
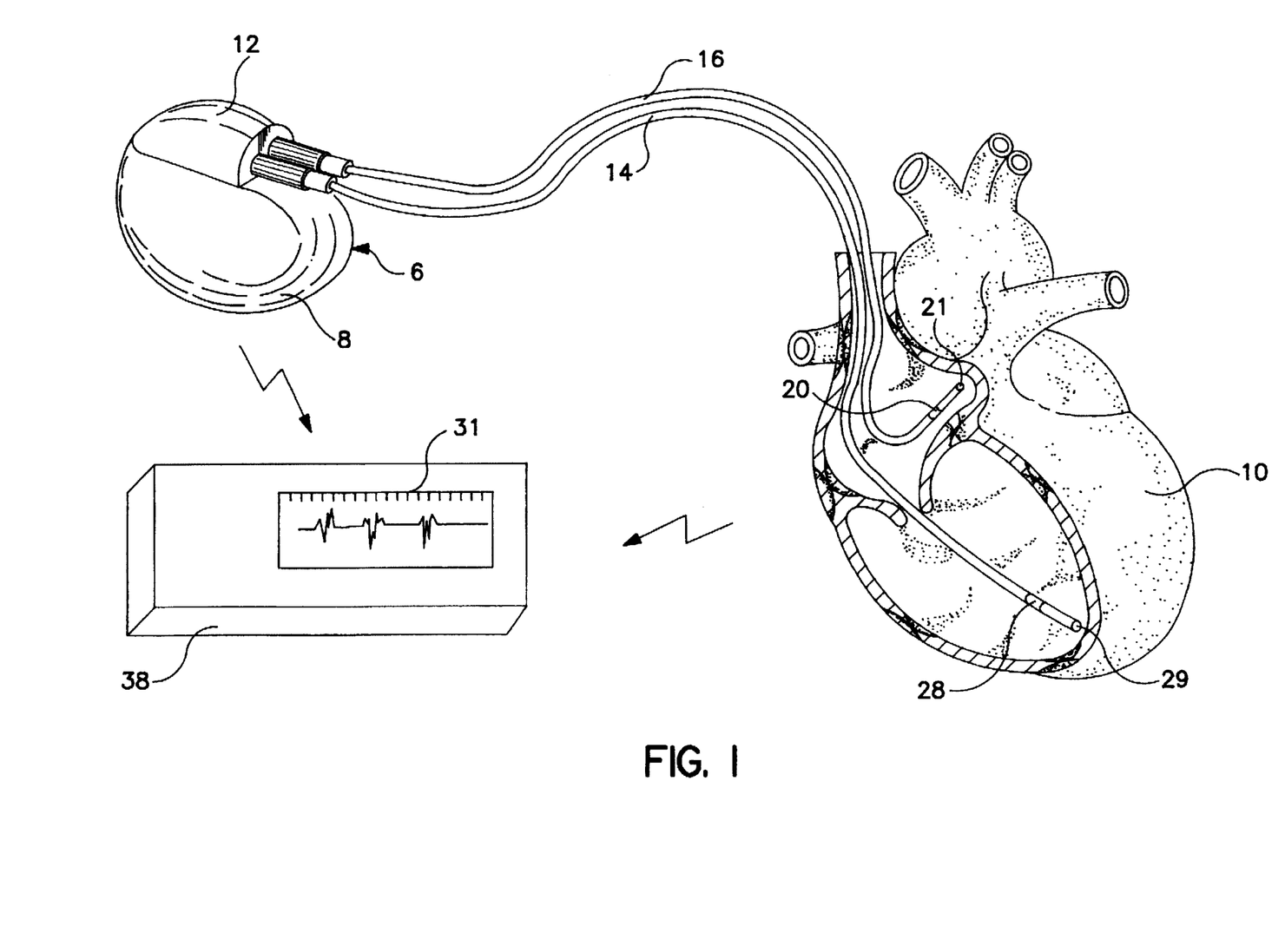
FIG. 1 is a perspective representation of a pacemaker system in accordance with this invention showing an implantable pacemaker connected to a patient's heart and an EKG strip recorder used to detect encoded pace pulse patterns during magnet mode.

FIG. 1 illustrates the external configuration of a dual chamber pacemaker 6, which is provided with a hermetically sealed enclosure 8, typically fabricated of biocompatible metal such as titanium. Although a dual chamber pacemaker is illustrated, it is to be understood that the invention is applicable to single chamber pacemakers as well. Mounted to the top of the enclosure 8 is a connector block assembly 12, which receives electrical connectors located on the proximal ends of leads 14 and 16. Lead 16 is an atrial pacing lead, carrying two electrodes 20 and 21. Electrodes 20 and 21 are used both to sense atrial depolarizations and to deliver atrial pacing pulses. Atrial pacing pulses may be delivered between electrode 20 and electrode 21 or between electrode 21 and the housing 8 of the pacemaker 6. Sensing of atrial depolarizations may occur between electrode 20 and electrode 21 or between either of electrode 20 and 21 and the housing 8 of the pacemaker 6.

Similarly, lead 14 represents a ventricular bipolar pacing lead, carrying two electrodes 28 and 29. As discussed above in conjunction with atrial lead 16, electrodes 28 and 29 are used to sense and pace the ventricle. Ventricular pacing may be accomplished between electrodes 29 and 28 or between electrode 29 and the conductive housing 8 of pacemaker 6. Sensing of ventricular signals, including depolarizations (QRS-waves) and repolarizations (T-waves) may be accomplished between electrodes 29 and 28 or between either of electrodes 29 and 28 and the housing 8 of the pacemaker 6. The pacemaker can operate in any desired mode, e.g., DDD, VDD, VVI, etc. However, when in magnet mode, it paces asynchronously, with a rate pattern that carries encoded data, as discussed more fully below. The pace pulses and patient heartbeats can be detected by hooking the patient to external apparatus 30, which contains an EKG strip recorder 31, as illustrated. Alternately, the device 30 may have a receiver for receiving signals transmitted from the pacemaker, and can analyze the magnet mode operation automatically, and/or provide a marker channel output for examination by the physician. Of course, device 30 may also be connected telephonically to a patient-operated programmer, to receive the magnet mode data.

Figure 2:
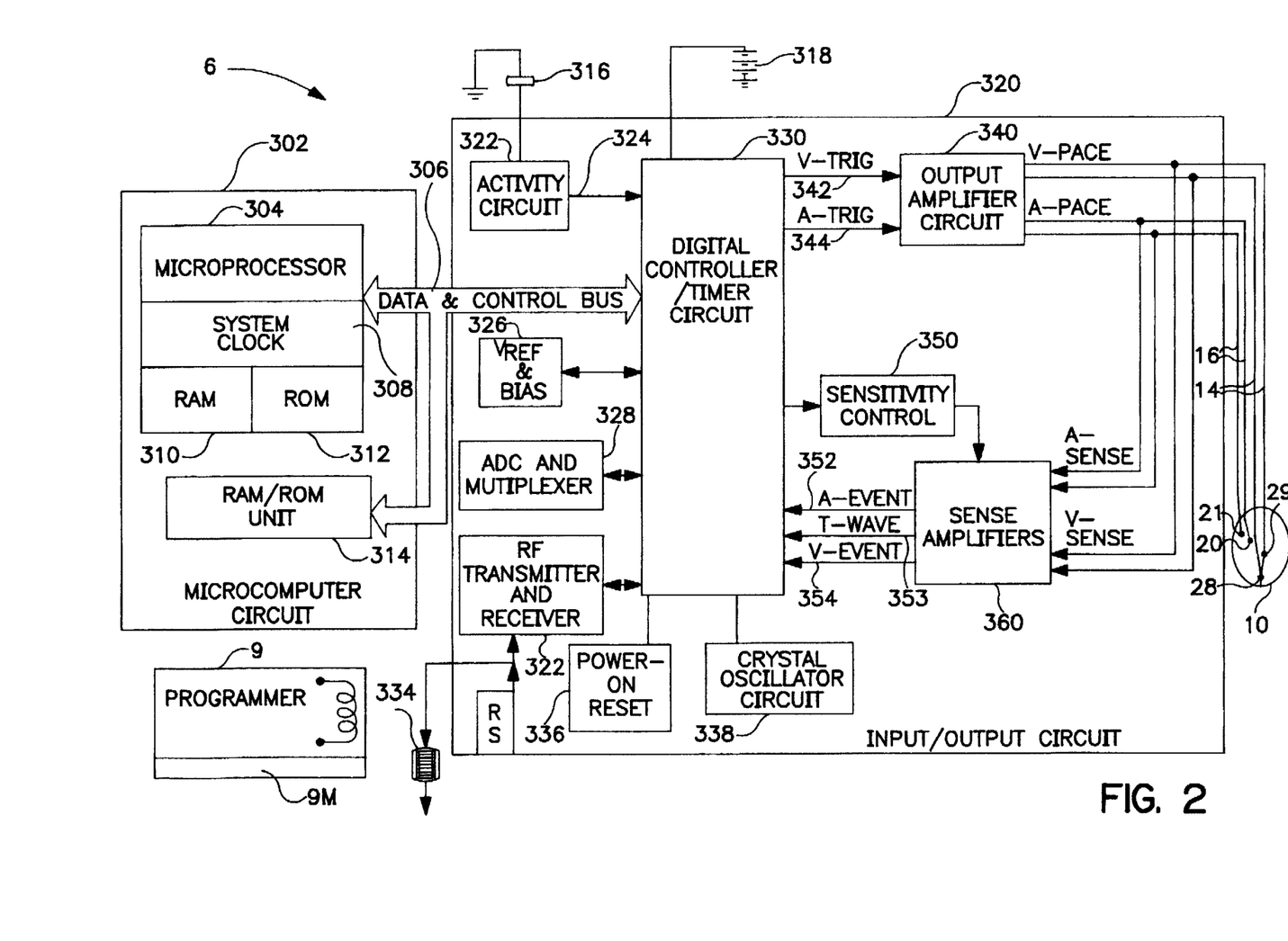
FIG. 2 is a block diagram of the primary functional components of a pacemaker system and method in accordance with this invention.

FIG. 2 is a block functional diagram of the pacemaker illustrated in FIG. 1, as connected to a human heart 10. The circuitry illustrated is all located within the conductive housing or can 8 of the pacemaker, as illustrated in FIG. 1, and the bipolar leads 14 and 16 are illustrated schematically as coupled directly to the circuit. However, of course, in the actual device they would be coupled by means of removable electrical connectors inserted in the connector block 12, as illustrated in FIG. 1.

The pacemaker is divided generally into a microcomputer circuit 302 and a pacing circuit 320. A pulse generator circuit 340 includes a ventricular pulse generator circuit coupled to the heart 10 by means of electrodes 29 and 28 on lead 14, as well as an atrial pulse generator circuit coupled to the heart 10 by means of atrial electrodes 20 and 21, located on lead 16. Similarly, pacing circuit 320 includes atrial and ventricular sense amplifiers in sense amplifier circuit 360, coupled to the atrium and ventricle by means of leads 14 and 16 as well. The ventricular sense amplifier provides for separate detection and identification of QRS-wave and T-wave signals, in a known manner. The output circuit 340 and sense amplifier circuit 360 may contain pulse generators and sense amplifiers corresponding to any of those presently employed in commercially marketed cardiac pacemakers. Control of timing and other functions within the pacemaker circuit is provided by digital controller/timer circuit 300, which includes a set of timers and associated logic. Digital controller/timer circuit 330 defines the basic pacing interval of the device, which may take the form of an A—A escape interval initiated on atrial sensing or pacing and triggering atrial pacing at the expiration thereof, or may take the form of a V—V escape interval, initiated on ventricular sensing or pacing and triggering ventricular pulse pacing at the expiration thereof. Digital controller/timer circuit 330 similarly defines the A–V escape interval, for synchronous pacing. The specific values of the intervals defined are controlled by the microcomputer circuit 302 by means of data and control bus 306. Sensed atrial depolarizations are communicated to the digital controller/timer circuit 330 on A event line 352; ventricular depolarizations (QRS-waves) are communicated to the digital controller/timer circuit 330 on V event line 354; and ventricular repolarizations (T-waves) are connected to circuit 330 on T-wave line 353. In order to trigger generation of a ventricular pacing pulse, digital controller/timer circuit 330 generates a trigger signal on V trig line 342. Similarly, in order to trigger an atrial pacing pulse, digital controller/timer circuit 330 generates a trigger pulse on a trig line 344. Memory 310, 312 are used to store routines and data which has been collected, e.g., pacemaker operating conditions and event data.

Digital controller/timer circuit 330 also defines time intervals for controlling operation of the sense amplifiers in sense amplifier circuit 360. Typically, digital controller/timer circuit 330 will define an atrial blanking interval following delivery of an atrial pacing pulse, during which atrial sensing is disabled, as well as ventricular blanking intervals following atrial and ventricular pacing pulse delivery, during which ventricular sensing is disabled. Digital controller/timer circuit 330 will also define an atrial refractory period during which atrial sensing is disabled, this refractory period extending from the beginning of the A–V escape interval following either a sensed or paced atrial depolarization, and extending until a predetermined time following sensing of a ventricular depolarization or delivery of a ventricular pacing pulse. Digital controller/timer circuit 330 similarly defines a ventricular refractory period following ventricular sensing or delivery of a ventricular pacing pulse, which is typically shorter than the portion of the atrial refractory period following ventricular sensing or pacing. Digital controller/timer circuit 330 also controls sensitivity settings of the sense amplifiers 360 by means of sensitivity control 350. This sensitivity control may be utilized to distinguish QRS-waves and T-waves. See U.S. Pat. No. 4,665,919, incorporated herein by reference. Although the pacemaker is illustrated as a dual chamber pacemaker, it is to be understood that the invention is equally applicable to single chamber pacemakers.

In the embodiment illustrated in FIG. 2, the pacemaker is provided with a piezo electric sensor 316 which is intended to monitor patient activity, in order to allow provision of rate responsive pacing, such that the defined pacing rate (A—A escape interval or V—V escape interval) increases with increased demand for oxygenated blood. Sensor 316 generates electrical signals in response to sensed physical activity which are processed by activity circuit 322 and provided to digital controller/timer circuit 330. Activity circuit 332 and associated sensor 316 may correspond to the circuitry disclosed in U.S. Pat. No. 5,052,388, issued to Betzold et al., and U.S. Pat. No. 4,428,378, issued to Anderson et al. incorporated herein by reference in their entireties.

Transmission to and from the external programmer 9 illustrated in FIG. 2 is accomplished by means of antenna 334 and associated RF transmitter and receiver 322, which serves both to demodulate received downlink telemetry and to transmit uplink telemetry. Crystal oscillator circuit 338 provides the basic timing clock for the circuit, while battery 318 provides power. Power on reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexor 328, power on reset circuit 336 and crystal oscillator circuit 338 may correspond to any of those presently used in current marketed implantable cardiac pacemakers. In a typical case, programmer 9 also has a magnet 9M, and the pacemaker also contains a reed switch RS, which is closed by the magnetic field of the magnet when the programmer is placed in vicinity of the pacemaker. Alternately, where no programmer is available, the magnet 9M alone may be placed adjacent the implanted pacemaker. The closing of the reed switch causes a signal to be inputted through receiver 332 into circuit 330, to initiate the magnet mode operation.

Microcomputer circuit 302 controls the operational functions of digital controller/timer 330, specifying which timing intervals are employed, and controlling the duration of the various timing intervals, via data and control bus 306. Microcomputer circuit 302 contains a microprocessor 304 and associated system clock 308 and on processor RAM circuits 310 and 312, respectively. In addition, microcomputer circuit 302 includes a separate RAM/ROM chip 314. Microprocessor 304 is interrupt driven, operating in a reduced power consumption mode normally, and awakened in response to defined interrupt events, which may include delivery of atrial and ventricular pacing pulses as well as sensed atrial and ventricular depolarizations. In addition, if the device operates as a rate responsive pacemaker, a timed interrupt, e.g., every cycle or every two seconds, may be provided in order to allow the microprocessor to analyze the sensor data and update the basic rate interval (A—A or V—V) of the device. In addition, in a preferred embodiment of the invention, the microprocessor 304 may also serve to define variable A-V escape intervals and atrial and ventricular refractory periods which may also decrease in duration along with decreases in duration of the basic rate interval. Specifically, the microprocessor is used to carry out the routines illustrated in FIGS. 4–7.

The illustrated circuitry of FIG. 2 is merely exemplary, and corresponds to the general functional organization of most microprocessor controlled cardiac pacemakers presently commercially available. It is to be understood that in many cases this invention may be practiced with less sophisticated pacemakers, and particularly pacemaker systems that do not have advanced telemetry systems.

Figure 3:
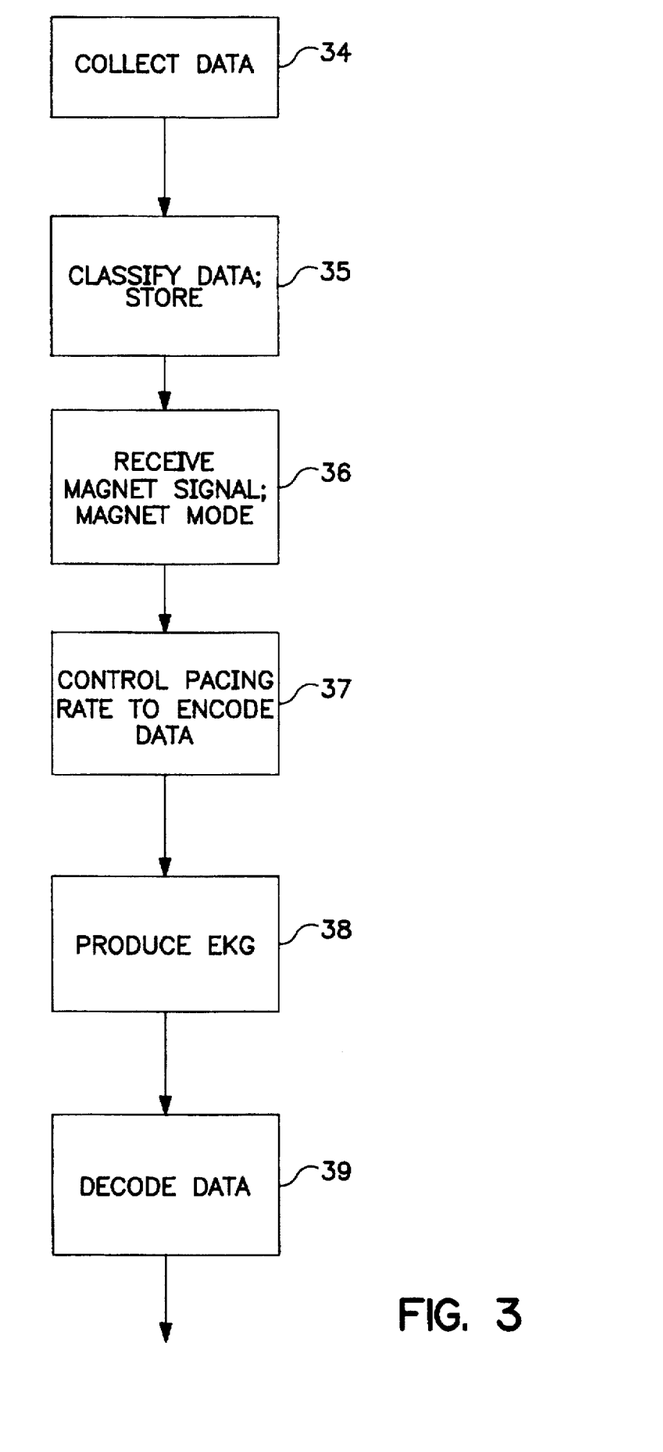
FIG. 3 is a flow diagram of the primary steps in transmitting data from an implanted pacemaker during magnet mode in accordance with this invention.

Referring now to FIG. 3, there is shown a flow diagram illustrating the primary operational steps of magnet mode operation in accord with this invention. As indicated at block 34, the pacemaker collects data, which may be a continuously ongoing procedure, and/or may be done in response to a programmed instruction. For example, battery condition is monitored by circuit 330, and a representation of battery condition, including ERI ("Elective Replacement Indicator") or EOL ("End of Life") is stored in memory. The pacemaker can also automatically test the leads by a known technique, and store an indication of "Atrial Lead suspect," or "Ventricular Lead suspect." In addition to various pacemaker conditions, event data is collected. Examples of event data include occurrences of Ventricular Tachycardia (VT), Atrial Tachycardia (AT), PACs, rate variations, percentages of paced and spontaneous events, and other diagnostic data. Some of this data can be classified, e.g., in histogram form, and the data is stored as shown at 35. At 36, the pacemaker receives a magnet signal, and goes into its magnet mode. Following this, at 37, the pacemaker controls the asynchronous pacing rate so as to encode stored data, as discussed further below.

As the encoded pacing intervals are generated, an EKG is produced at 38, on which the magnet mode rate behavior can be seen by a physician. Switching magnet rates in the range of 85–105 bpm, for example, is safe and provides capability for transmission of significant data. Thus, for a standard EKG chart-paper speed of 25 mm/sec, a difference in intervals of about 30–40 ms can be easily discerned. The difference between intervals for 85 and 90 ppm is 39 ms; for 90 and 95, 35 ms; for 95 and 100, 32 ms; and 100 and 106, 29 ms. Thus, changes in V—V or A—A intervals having 5 ppm differences within the 85–105 range can be determined from a standard strip chart. In addition, smaller interval differences can be detected from an EKG strip, particularly where bracketed with standard intervals so that the data-carrying intervals are easily identified. Thus, the "decode data" step indicated at block 39 can be done by the physician in most applications of this invention, with or without calipers to decipher the data.

While the decoding is done by a person in the preferred embodiments, it is to be noted that the invention also includes machine decoding of the rate patterns. Thus by, merely assuring that the decoding machine has a way to recognize and time pacing pulses it can figure the rates and display a message that directly corresponds to the rate by means of a look up table, stored in the machine's memory.

Various routines that meet the above criteria can be stored in memory 310, 312 and operated under the control of microprocessor 304. For example, a standard magnet rate of 85 ppm can be repeated for a defined number of intervals, e.g., 4. Following this, for the next several intervals, e.g., 3, rates 90, 95 or 100 are used in different combinations, so that 27 combinations are available over 3 intervals. Note that for this example, the smallest interval change is 32 ms (between 95 and 100 ppm), while the largest is 100 ms (85 and 100 ppm). Of course, more data can be encoded by using more different rates, and more data intervals. Thus, four different rates, over 4 intervals, yields 256 combinations. In practice, the number of combinations used may suitably be on the order of only 8–32, so that a reference card can be used by the physician for decoding. For example, an arrangement of 16 combinations can encode the yes/no status of each of four independent conditions, and can be provided by four possible rates and two encoded intervals; one or more additional intervals can be used to encode additional data relating to one or more of the conditions. As a specific example, consider four independent variables, or conditions, namely Atrial Tachycardia, Ventricular Tachycardia, Atrial Lead Integrity, and Ventricular Lead Integrity. Using two coded intervals, the following encoding scheme is illustrative.

| 85 | 85 | 85 | 85 | 90  | 90  | all OK |
|----|----|----|----|-----|-----|--------|
| 85 | 85 | 85 | 85 | 90  | 95  | Atrial Tachycardia |
| 85 | 85 | 85 | 85 | 90  | 100 | Ventricular Tachycardia |
| 85 | 85 | 85 | 85 | 90  | 105 | Atrial Tachycardia and Ventricular Tachycardia |
| 85 | 85 | 85 | 85 | 95  | 90  | Atrial Lead suspect |
| 85 | 85 | 85 | 85 | 95  | 95  | Atrial Lead suspect, and Atrial Tachycardia |
| 85 | 85 | 85 | 85 | 95  | 100 | Atrial Lead suspect, and Ventricular Tachycardia |
| 85 | 85 | 85 | 85 | 95  | 105 | Atrial Lead suspect and Atrial and Ventricular Tachycardia |
| 85 | 85 | 85 | 85 | 100 | 90  | Ventricular Lead suspect |
| 85 | 85 | 85 | 85 | 100 | 95  | Ventricular Lead suspect, and Atrial Tachycardia |
| 85 | 85 | 85 | 85 | 100 | 100 | Ventricular Lead suspect, and Ventricular Tachycardia |
| 85 | 85 | 85 | 85 | 100 | 105 | Ventricular Lead suspect, and Atrial and Ventricular Tachycardia |
| 85 | 85 | 85 | 85 | 105 | 90  | Atrial and Ventricular Lead suspect |
| 85 | 85 | 85 | 85 | 105 | 95  | Atrial and Ventricular Lead suspect, and Atrial Tachycardia |
| 85 | 85 | 85 | 85 | 105 | 100 | Atrial and Ventricular Lead suspect, and Ventricular Tachycardia |
| 85 | 85 | 85 | 85 | 105 | 105 | Atrial and Ventricular Lead suspect, and Atrial and Ventricular Tachycardia |

Figure 4:
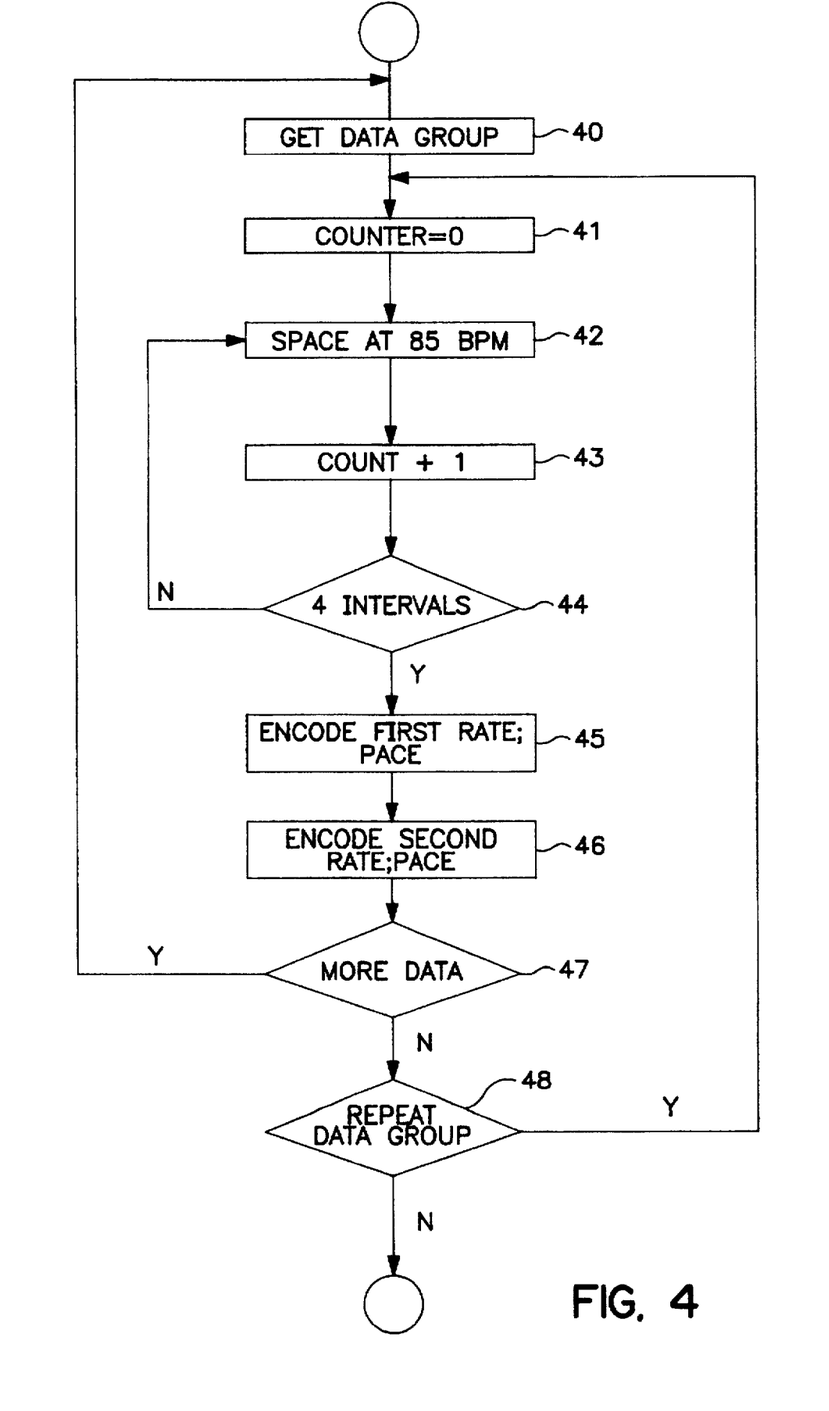
FIG. 4 is a flow diagram of a first embodiment for varying rate when in magnet mode, so as to transmit data encoded as pace pulse rate variations that are seen on an EKG strip.

This arrangement is illustrated in FIG. 4. At 40, the pacemaker gets from memory a data group, e.g., the yes/no status of each of the four conditions. At 41, a counter is set to 0. At 42, the pacemaker paces at 85, and then at 43 the count is incremented. At 44 it is determined whether the count equals 4; if not, the routine loops until four pace pulses have been delivered at intervals corresponding to 85 ppm. Then, at 45, a first rate is selected as one of the four possible rates, and the first data-encoded pace pulse is delivered at a corresponding interval. At 46, the second rate is selected, and the second data-encoded pulse is delivered at the rate corresponding to the data. At 47, the routine determines whether there is more data to deliver, e.g., data representative of other conditions, or more data concerning the first conditions. If yes, the routine returns to block 40; if not, it goes to 48, and determines whether the same data group is to be repeat-transmitted, for redundancy. If yes, the routine goes back to block 41.

Figure 5:
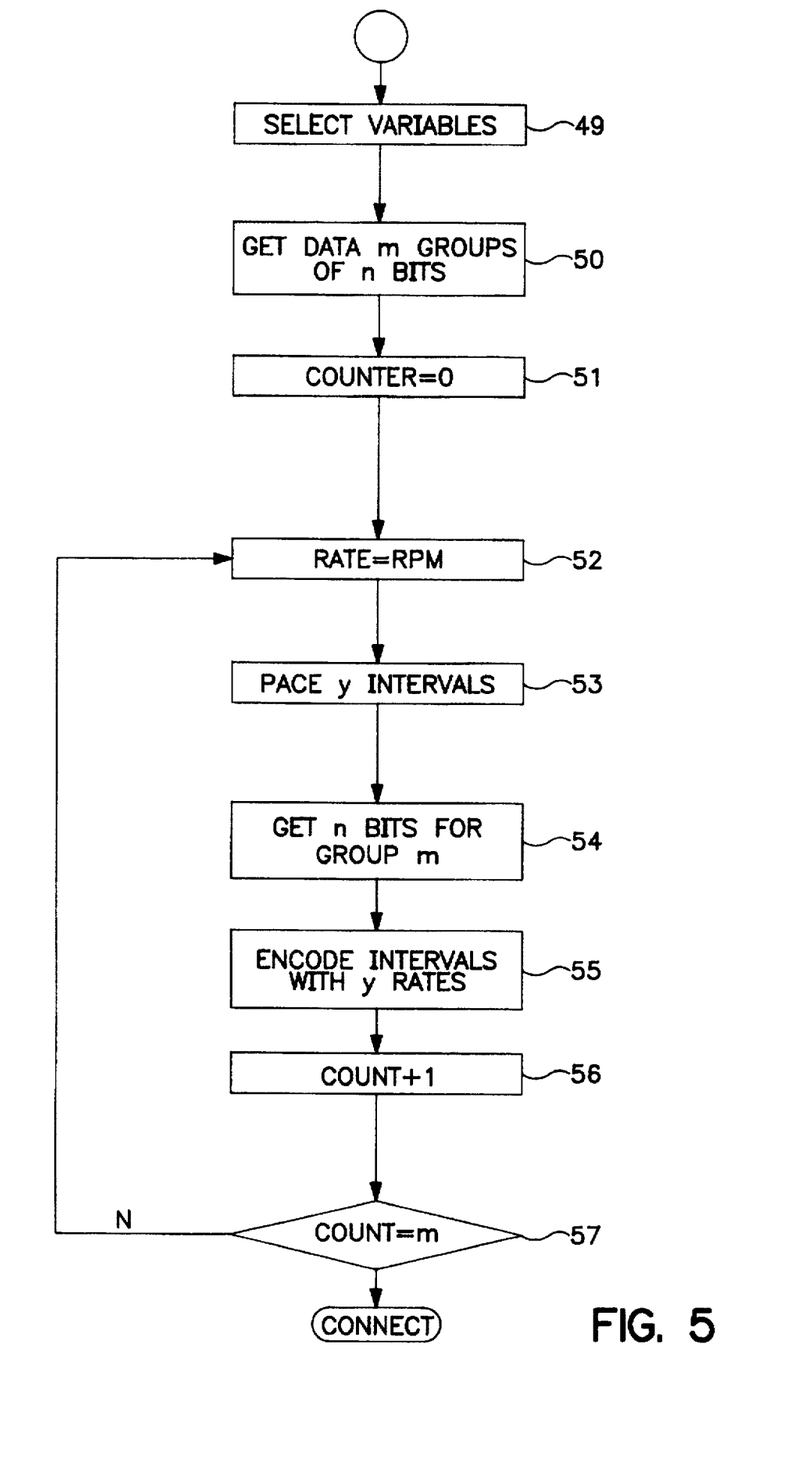
FIG. 5 is a flow diagram of a more general encoding scheme in accordance with this invention.

Referring now to FIG. 5, there is shown a routine which covers more combinations of data-encoded intervals which are positioned after or between intervals at a standard rate. The use of standard rate intervals enables maintaining a substantially constant rate, which minimizes patient discomfort; and also frames the data-encoded intervals so that they can be more easily identified. At 50, the pacemaker goes to memory and gets m groups of n bits of data. For example, the data may represent three groups, each having 16 bits, or combinations. At 51, a counter is set to zero. At 52, a rate R is set, e.g., 85 ppm. At 53, the pacemaker delivers y intervals (e.g., 4) at the selected rate R. Then, at 54, the pacer gets the n data bits for group m, where m is determined by the counter. At 55, the data is encoded over x intervals, where x can be any selected number, with one of y rates, such that y rates over x intervals yields n combinations. After this, the count is incremented at 56, and at 57 it is determined if count=m. If not, the routine returns to 52, and repeats the sequence from 52–55 for sending successive groups of data.

Other encoding algorithms are within the scope of the invention. For example, the rate sequence may be of the form "85,85,85,85,A,85,B,85,C,85,D,85,E, . . . ", where each respective A–E interval is a data-encoded interval between two limits corresponding to two rates. Thus, if the rate limits are 90 and 105 ppm, then each data-encoded interval has one of a predetermined number of values between the limits of 667 and 571 ms. For example, for 4 possible values, increments of about 33 ms can be used to represent the data; for 5 possible values, increments of about 24 ms can be used; smaller increments would provide a larger number of values, but would probably require machine decoding. The algorithm includes a predetermined order of the data intervals, e.g. data interval A can contain information about Atrial Tachycardia; data interval B corresponds to Ventricular Tachycardia; data interval C corresponds to the number of PVCs; D corresponds to measured battery voltage; etc. If other sensors are used for other indications, like local measures of impedence, long term oxygen saturation trends or the like, other data intervals (E,F,G etc.) could be used for these or other indications of implant state or patient condition reporting.

There has thus been provided a system and method of transmitting increased data from an implanted pacemaker when in magnet mode. The invention enables a relatively simple means of providing a physician data from the pacemaker without the need to have a programmer on hand to receive the data. This system meets a need that exists for less sophisticated pacemaker systems which do not have telemetry capability, or for the situation where the patient is in a remote location where the physician does not have a programmer, but relies solely on a magnet for doing pacemaker follow-ups. The invention as claimed provides for increased data transmission capability during magnet mode by encoding pacemaker data, e.g., data representative of pacemaker conditions, pacing events and patient event data, in sequences of selected pacing intervals.

I claim:

1. An implantable pacemaker having pace pulse means for delivering pace pulses to a patient at a controllable rate, data means for collecting pacemaker data representative of at least one of a group of selected pacemaker operating conditions and events, and receiving means for receiving a request from an external source for at least some of said data, comprising responding means for responding to a said request, said responding means having rate adjusting means for adjusting the pacing rate of delivered pace pulses, said adjusting means having control means for controlling said pulse means to deliver pace pulses with a pattern of pacing intervals, at least a fraction of said pace pulses each being independently adjusted to one of a plurality of predetermined rates so that said fraction carries said requested data.

2. The pacemaker as described in claim 1, wherein said receiving means has magnetic means for receiving a magnet-generated request.

3. The pacemaker as described in claim 1, wherein said pacemaker operating conditions include battery condition and pace pulse threshold, and said pacemaker has battery test means for testing said battery and determining a measure of remaining battery lifetime, and threshold test means for determining the threshold to delivered pace pulses.

4. The pacemaker as described in claim 1, wherein said data means comprises means for collecting data representative of events including atrial tachycardia, ventricular tachycardia, atrial lead integrity and ventricular lead integrity.

5. The pacemaker as described in claim 1, wherein said adjusting means has means for adjusting the rate of each of a fraction m of said pattern of pace pulses to a selected one of n rates, and encoding means for encoding said adjusted rates in accordance with said requested data.

6. The pacemaker as described in claim 1, wherein said control means has means for controlling some of said pace pulses of said pattern to be delivered at a given rate, and selected ones of said pace pulses to be delivered at adjusted rates encoded with said requested data.

7. The pacemaker as described in claim 6, wherein said controlling means has pattern means for controlling delivery of a pattern of pace pulses comprising subpatterns of x successive pace pulses at a given rate, each followed by m successive pace pulses encoded with one of n different rates.

8. The pacemaker as described in claim 7, wherein said adjusting means adjusts the rate of each said encoded pace pulse to one of a plurality of selected rates which are at least 5 bpm apart.

9. The pacemaker as described in claim 6, wherein said control means controls delivery of a pattern of intervals comprising one or more predetermined intervals at a rate representative of a condition or event, and succeeding intervals carrying information relating to each said condition or event.

10. A pacemaker having a pulse generator for generating pacing pulses at a controllable rate, storage means for storing pacemaker data, rate control means for controlling pacing rate to one of a predetermined plurality of discrete rates, said discrete rates corresponding to readable pacing intervals on a standard EKG strip recorder, and said rate control means having data encoding means for encoding said pacemaker data by adjusting each of a plurality of pacing intervals to one of said discrete rates, each of said intervals representing data independently of the other, whereby said plurality of intervals is encoded with said data so that it can be determined from an EKG strip recorder.

11. The pacemaker as described in claim 10, wherein said data encoding means further has means for interspersing said plurality of discrete rate intervals with pacing intervals at a given rate, whereby said encoded intervals can be better perceived on an EKG strip chart.

12. The pacemaker as described in claim 10, wherein said storage means has means for storing event data and value data associated with said event data, and said data encoding means has event means for encoding the occurrence of a given event and value means for encoding a value associated with said event.

13. A method of transmitting pacemaker data from an implanted pacemaker which is in magnet mode, comprising:

delivering a pattern of pace pulses at different intervals corresponding to predetermined discrete rates, said pattern including a combination of data-encoded pace pulses, each of said data-encoded pace pulses being at a selected one of a predetermined number of rates, and interspersing said data-encoded pace pulses with pace pulses at a predetermined rate.

14. The method as described in claim 13, comprising printing out an EKG on a strip recorder while said pattern of pace pulses is being delivered.

15. The method as described in claim 14, further comprising the step of decoding said pacemaker data from said strip recorder EKG by determining the intervals of the data-encoded pace pulses.

16. The method as described in claim 13, wherein said delivering of said pattern of pace pulses comprises delivering data-encoded pace pulses and predetermined rate pace pulses in accordance with a predetermined sequence.

* * * * *